US008404228B2

(12) United States Patent
Gorbach et al.

(10) Patent No.: US 8,404,228 B2
(45) Date of Patent: *Mar. 26, 2013

(54) FOOD CONTAINING A PROBIOTIC AND AN ISOLATED β-GLUCAN AND METHODS OF USE THEREOF

(76) Inventors: Sherwood L. Gorbach, Weston, MA (US); Barry R. Goldin, West Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/184,959

(22) Filed: Jul. 18, 2011

(65) Prior Publication Data

US 2011/0274722 A1    Nov. 10, 2011

Related U.S. Application Data

(63) Continuation of application No. 11/884,187, filed as application No. PCT/US2006/005271 on Feb. 15, 2006, now Pat. No. 7,981,412.

(60) Provisional application No. 60/652,935, filed on Feb. 15, 2005.

(51) Int. Cl.
*A01N 63/00* (2006.01)
*A23K 1/00* (2006.01)

(52) U.S. Cl. ..................... 424/93.45; 426/615

(58) Field of Classification Search .................. None
See application file for complete search history.

(56) References Cited

U.S. PATENT DOCUMENTS

| | | | | |
|---|---|---|---|---|
| 4,839,281 | A * | 6/1989 | Gorbach et al. ............ | 435/34 |
| 4,874,618 | A | 10/1989 | Seaborne et al. | |
| 6,241,983 | B1 * | 6/2001 | Paul et al. .................. | 424/93.4 |
| 6,835,558 | B2 | 12/2004 | Van Lengerich et al. | |
| 7,033,629 | B2 | 4/2006 | Koss et al. | |
| 7,101,565 | B2 * | 9/2006 | Monte ...................... | 424/423 |
| 7,981,412 | B2 * | 7/2011 | Gorbach et al. ........... | 424/93.45 |
| 2002/0150658 | A1 * | 10/2002 | Morrissette et al. ........ | 426/120 |
| 2003/0147857 | A1 | 8/2003 | Monte | |
| 2005/0272694 | A1 | 12/2005 | Moriya et al. | |
| 2006/0165670 | A1 | 7/2006 | Beer et al. | |

FOREIGN PATENT DOCUMENTS

| | | |
|---|---|---|
| DE | 202 02 562 | 5/2002 |
| EP | 0 568 530 | 11/1993 |
| JP | 2003-274852 | 9/2003 |
| WO | WO 91/17672 | 11/1991 |
| WO | WO 9826787 | 6/1998 |
| WO | WO 0033854 | 6/2000 |

OTHER PUBLICATIONS

Jaskari et al. Appl. Microbiol. Biotechnol., 1998, 49: 175-181.*
Bekers et al. Food technology. 2001, 15(1):1-12.*
Bekers et al., "Oats and Fat-Free Milk Based Functional Food Product," *Food Biotechnology* 15:1-12, 2001.
Bezkorovainy, "Probiotics: Determinants of Survival and Growth in the Gut[1-3]," *Am. J. Clin. Nutr.* 73:399S-405S, 2001.
Charalampopoulos et al., "Application of Cereals and Cereal Components in Functional Foods: A Review," *Int. J. Food Microbiol.* 79:131-141, 2002.
Corcoran et al., "Comparative Survival of Probiotic *Lactobacilli* Spray-Dried in the Presence of Prebiotic Substances," *J. Appl. Microbiol.* 96:1024-1039, 2004.
Declaration of Dr. Barry R. Goldin filed in European Application No. 06735092.6, dated Jul. 15, 2009.
Dongowski et al., "Dietary Fiber-Rich Barley Products Beneficially Affect the Intestinal Tract of Rats," *J. Nut.* 132: 3704-3714, 2002.
Femia et al., "Antitumorigenic Activity of the Prebiotic Inulin Enriched with Oligofructose in Combination with the Probiotics *Lactobacillus rhamnosus* and *Bifidobacterium lactis* on Azoxymethane-Induced Colon Carcinogenesis in Rats," *Carcinogenesis* 23:1953-1960, 2002.
Heller, "Probiotic Bacteria in Fermented Foods: Product Characteristics and Starter Organisms[1-3]," *Am. J. Clin. Nutr.* 73:374S-379S, 2001.
Jaskari et al., "Oat β-Glucan and Xylan Hydrolysates as Selective Substrates for *Bifidobacterium* and *Lactobacillus* Strains," *Appl. Microbiol. Biotechnol.* 49:175-181, 1998.
Kontula et al., "Oat Bran β-gluco- and Xylo-Oligosaccharides as Fermentative Substrates for Lactic Acid Bacteria," *Int. J. Food Microbiol.* 45:163-169, 1998.
Kontula, "In Vitro and In Vivo Characterization of Potential Probiotic Lactic Acid Bacteria and Prebiotic Carbohydrates," *Finnish J. Dairy Science* 54:1-142, 1999 (Abstract only).
Marchesini et al., "Branched-Chain Amino Acid Supplementation in Patients with Liver Diseases," *J. Nutr.* 135:1596S-1601S, 2005.
Megazyme, "Mixed-Linkage Assay Procedure (McCleary Method)," 1-16, 2006.
Osman et al., "Modulation of the Effect of Dextran Sulfate Sodium-Induced Acute Colitis by the Administration of Different Probiotic Strains of *Lactobacillus* and *Bifidobacterium*," *Dig. Dis. Sci.* 49:320-327, 2004.
Rayes et al., "Supply of Pre- and Probiotics Reduces Bacterial Infection Rates After Liver Transplantation—A Randomized, Double-Blind Trial," *Am. J. Trans.* 5:125-130, 2005.
Roller et al., "Prebiotic Inulin Enriched with Oligofructose in Combination with the Probiotics *Lactobacillus rhamnosus* and *Bifidobacterium lactis* Modulates Intestinal Immune Functions in Rats," *J. Nutr.* 134:153-156, 2004.
Saarela et al., "Fibres as Carriers for *Lactobacillus rhamnosus* During Freeze-Drying and Storage in Apple Juice and Chocolate-Coated Breakfast Cereals," *Int. J. Food Microbiol.* 112:171-178, 2006.
Skendi et al., "Structure and Rheological Properties of Water Soluble β-Glucans from Oat Cultivars of *Avena sativa* and *Avena bysantina*," *J. Cereal Sci.* 38:15-31, 2003.
Stadler et al., "Optimization of a Formulation Containing Viable Lactic Acid Bacteria," *Int. J. Pharm.* 256:117-122, 2003.

(Continued)

*Primary Examiner* — Vera Afremova
(74) *Attorney, Agent, or Firm* — Clark & Elbing LLP; Todd Armstrong

(57) ABSTRACT

The invention features a food product containing a probiotic and β-glucan isolated from a natural source, methods of treating a disease or disorder by administering the food product, and a package containing separated components of the food product.

28 Claims, No Drawings

OTHER PUBLICATIONS

Topping et al., "Session: Nutrients Contributing to the Fibre Effect; Resistant Starch as a Prebiotic and Synbiotic: State of the Art," *Proc. Nut. Soc.* 62:171-176, 2003.

Xing et al., "Intestinal Microflora in Rats with Ischemia/Reperfusion Liver Injury," *J. Zhejiang Univ. SCI* 6B:14-21, 2005.

* cited by examiner

FOOD CONTAINING A PROBIOTIC AND AN ISOLATED β-GLUCAN AND METHODS OF USE THEREOF

CROSS-REFERENCE TO RELATED APPLICATIONS

This application is a continuation of U.S. Ser. No. 11/884,187, filed Aug. 10, 2007, which is the U.S. National Stage of PCT/US2006/05271, filed Feb. 15, 2006, which claims benefit of U.S. Provisional Application Ser. No. 60/652,935, filed Feb. 15, 2005.

FIELD OF THE INVENTION

The present invention relates to the field of probiotic products.

BACKGROUND OF THE INVENTION

Probiotics are microbial organisms that are associated with beneficial health effects and may be used for the prevention and treatment of diseases. Lactic acid bacteria, such as *bifidobacteria* and *lactobacilli*, are probiotics that are beneficial in treating conditions such as diarrhea, food allergies, dental caries, and respiratory infections, and also find use as vaccine adjuvants.

When administered exogenously, probiotics can survive in sufficient numbers to affect gut microbial metabolism, although survival rates are limited to 20-40%. The main obstacles to probiotic survival in the gut include gastric acidity and the action of bile salts. Certain exogenously administered substances can enhance the action of both exogenous and endogenous probiotics. For instance, human milk can stimulate the growth of *bifidobacteria* in vitro and also in the small intestine of infants; however, it is unlikely that they function in the colon. Lactulose and certain fructose-containing compounds, called prebiotics, are not digested in the small intestine but pass into the colon unaltered, where they can be selectively utilized by probiotics. Beneficial effects may thus accrue from exogenously administered probiotics when administered with prebiotics. Oligofructose and other complex sugars such as oligoxylans, oligoarabinoxylans, and raffinose, however, cannot be metabolized by certain *lactobacilli*, and therefore, these prebiotics cannot support the growth of such organisms.

*Lactobacillus* is a type of lactic acid bacteria which is used to ferment milk products to produce yogurt, buttermilk, and cheeses. *Lactobacilli* are considered probiotics because of their health benefits and are generally recognized as safe (GRAS). The first systematic scientific investigations on the health benefits of *Lactobacillus* were conducted 100 years ago. The *Lactobacillus rhamnosus* strain GG (LGG; ATCC Accession No. 53103) is an optimal probiotic strain because of its ability to survive stomach acid and bile, and proceed intact to the intestines. LGG has been shown to be beneficial in treating a number of medical conditions including acute infectious diarrhea in children and adults, antibiotic-associated diarrhea, traveler's diarrhea, infant food allergies, vaccine adjuvants, dental caries, and acute respiratory infections.

It is common practice in commercial production of *Lactobacillus* probiotics to mix the bacterial strain with prebiotics such as oligofructose or inulin. Laboratory investigations, however, have established that these prebiotics are not well metabolized by LGG and therefore do not support the growth of this organism. It has also been shown that LGG cannot effectively metabolize other complex sugars such as oligoxylans, oligoarabinoxylans, and raffinose.

SUMMARY OF THE INVENTION

The invention features edible compositions (i.e., foods) and medicaments such as topical creams, ointments, capsules and pills as well as suppositories that include a probiotic and an isolated β-glucan. Foods of the invention include orally-ingested, health promoting substances including chewable foods, beverages, tablets, capsules, and powders.

In a preferred embodiment, the edible composition is a dairy product (e.g., solid and liquid yogurt products, cottage cheese, milk drinks, and powdered milk products). In other preferred embodiments, the edible composition is an infant food (e.g., infant formula and infant cereal).

Preferred probiotics include gut colonizing bacteria such as *lactobacillus* bacteria, especially members of the genus *Lactobacillus*. Exemplary members of *Lactobacillus* include *Lactobacillus rhamnosus* (e.g. *Lactobacillus rhamnosus* GG), *Lactobacillus acidophilus*, *Lactobacillus brevis*, *Lactobacillus bulgaricus*, *Lactobacillus casei*, *Lactobacillus casei* subsp. *casei*, *Lactobacillus catenaforme*, *Lactobacillus delbrueckii*, *Lactobacillus delbrueckii* subsp. *bulgaricus*, *Lactobacillus fermentum*, *Lactobacillus gasseri*, *Lactobacillus iners* subsp. *nov*, *Lactobacillus jensenii*, *Lactobacillus johnsonii*, *Lactobacillus lactis*, *Lactobacillus leichmannii*, *Lactobacillus paracasei*, *Lactobacillus plantarum*, *Lactobacillus reuteri*, and *Lactobacillus salivarius*.

β-glucans can support an increased growth rate of *lactobacillus* bacteria, in particular LGG, in food, and can do so without the sometimes unwanted effects that growth promotion using glucose can entail. β-glucans can be isolated from a variety of plant sources, according to known techniques, e.g., those described in U.S. Pat. No. 6,835,558, hereby incorporated by reference. In preferred embodiments, β-glucan is isolated from cereals such as oat, barley, wheat, rye, maize, quinoa, millet, buckwheat, rice, wild rice, or spelt. In another preferred embodiment, β-glucan is isolated from yeasts, mushrooms, or other fungi. β-glucan that is isolated from a natural source for use in the invention need not be purified to homogeneity; it must only be more pure than as it occurs in nature. In preferred embodiments, the β-glucan isolated from a natural source is at least 10%, 20%, 30%, or 40% pure by weight, more preferably at least 50%, 60%, 70% or 80% pure by weight, and most preferably 90%, 95%, or 99% pure by weight.

β-glucans are indigestible (to humans) glucooligomers in which one or more of the glucose units are linked by β-linkages. β-glucans isolated from natural sources generally have either three or four glucose units; these forms are designated, respectively, $GLC_3$ and $GLC_4$. In another preferred embodiment, substantially unfermented β-glucan is mixed with the probiotic to form foods of the invention. In another preferred embodiment, foods of the invention contain substantially unfermented β-glucan prior to consumption.

As is mentioned above, food products of the invention may include solid or liquid foods. Exemplary foods include, but are not limited to, dairy products such as yogurt, butter, cheese, infant formula, or ice cream. Edible compositions may also be in the form of liquid, evaporated, condensed, or dry milk. Any composition of the invention may also include non-dairy liquid or solid food products, whey protein, flavors or flavor masking agents, sweeteners, and vitamins or dietary supplements.

In other embodiments, the food product is maintained at less than room temperature, preferably less than 25° C., more preferably less than 16° C., and most preferably 4° C. or less.

In another embodiment, the invention features a packaged food product that includes at least a first and a second compartment isolated from each other by an intermediate partition or seal that prevents mixing of the contents of the compartments. The first compartment includes a composition containing a probiotic and the second compartment includes a composition containing an isolated β-glucan. The package is constructed to permit mixing of the two compositions in the package, e.g., by a consumer prior to consumption of the mixed food product. The package can include a tube with at least two compartments that are separated by a seal that is more readily broken than the seal forming the periphery of the package, i.e., a "burst" seal. After purchase by the consumer, the consumer applies sufficient pressure to the tube to burst the seal separating the two compartments. Once the seal is broken, the two compositions in the separate compartments can be mixed by the consumer. In a preferred embodiment, the β-glucan-containing composition is maintained in a dry state, such as in powder form. In another preferred embodiment, the probiotic-containing composition is a liquid or semi-solid food. In other preferred embodiments, the probiotic-containing composition is a dairy or non-dairy food. In yet other embodiments, the probiotic-containing composition is yogurt, butter, cheese, infant formula, or ice cream.

The foods of the invention can be used, generally, for treatment of many medical conditions. Treatment, generally, involves simply ingesting a sufficient amount of the food to provide a health benefit. Gut disorders are particularly amenable to treatment with foods of the invention. Exemplary gut disorders include irritable bowel syndrome, inflammatory bowel disease, stomach ulcers, pouchitis, diarrhea, and *Heliobacter pylori* infection.

Foods of the invention can also be used to reduce allergic conditions, including atopic eczema, asthma, seasonal or perennial allergic rhinitis, pollen, dust, or mold allergies, and food allergies (e.g. lactose allergies).

Foods of the invention can also be used to reduce the colonization of mucosal tissues by pathogenic bacteria. Exemplary mucosal tissues include those lining the gastrointestinal tract, respiratory tract, nasal cavity, oral cavity, vagina, rectum, urethra, or lungs.

Foods of the invention can also be used to promote a more healthful balance of the bacterial flora of the gut.

Foods of the invention can also be used as adjuvants, enhancing immune responses to vaccines.

By "cereal" is meant the grains of grasses such as oats, barley, wheat, rye, maize, quinoa, millet, buckwheat, rice, wild rice, or spelt.

By "gut disorder" is meant any condition that causes gastrointenstinal distress. Conditions include adult or infant diarrhea, irritable bowel syndrome, inflammatory bowel disease, pouchitis, stomach ulcers, or infection by pathogens such as *Heliobacter pylori, Staphylococcus, Enterococcus*, or any other bacterial, fungal, viral, or protozoan parasite. Diarrhea may be caused by microbial enteropathogen infection. Exemplary enteropathogens include, but are not limited to *Clostridium difficile, Escherichia coli, Bacillus, Campylobacter, Shigella, Salmonella, Vibrio cholera, Yersinia, Giardia, Entamoeba histolytica, Cryptosporidium, Cyclospora*, or any other bacterium, virus, protozoa, or parasite that enters the gastrointenstinal tract. Diarrhea may also be associated with antibiotic administration, HIV infection, or radiation therapy.

By "substantially unfermented β-glucan" is meant that less than 10% by weight of the β-glucan used to prepare foods of the invention has undergone fermentation, which is the anaerobic conversion of sugar to carbon dioxide and alcohol. In preferred embodiments, less than 5% by weight, and more preferably less than 1% by weight, of the β-glucan has undergone fermentation.

DETAILED DESCRIPTION

According to the invention, isolated β-glucans from plants such as oats, barley, and mushrooms can be metabolized to support the growth, of the probiotic *Lactobacillus rhamnosus* strain GG (LGG). β-glucans admixed with LGG can increase the intestinal colonization and numbers of LGG in the bowel when administered orally in the form of foods such as drinks, cheeses, dairy products, baby formulas, and baby cereals, and medicaments in the forms of capsules or tablets. Accordingly, the effectiveness of LGG in preventing or treating medical conditions and improving well-being is enhanced. The combination of the probiotic LGG with a prebiotic β-glucan designed to enhance the growth of LGG in the gastrointestinal tract and at other mucosal surfaces such as the respiratory tract, genital tract, nasal cavity, oral cavity, rectum, urethra, or lungs provides an effective combination to improve the efficacy and uses of the probiotic organism LGG.

The necessary daily ingestion of β-glucan to exert a prebiotic effect and increase the numbers of LGG is between 2 to 8 grams/day. This level of β-glucan cannot be attained by ingestion of the native food stuffs such as oats or barley. Bulk β-glucan can be obtained from, e.g., AHD International, NURTURE®, Inc., and QUAKER® Oats Company.

The numbers of LGG required to attain a probiotic health benefit is between $10^7$ and $10^{10}$ bacteria ingested daily. Therefore an effective amount of a food product that would result in an enhanced probiotic health effect includes about 10 to 100 ml or 10 to 100 grams of a yogurt, drink, food, cheese, or baby formula which contains between about $10^6$ and $10^8$ LGG bacteria per ml or between about $10^6$ and $10^8$ LGG bacteria per gram, or a capsule, tablet or suppository containing about 10 mg to 100 mg lypholized LGG powder containing $10^9$ to $10^{11}$ LGG per gram, or an ointment that contains about 10 mg to 100 mg of lypholized LGG powder containing about $10^9$ to $10^{11}$ LGG per gram. Any of these compositions will also include about 0.5 to 8 grams of β-glucan isolated from a natural source. For adult consumers of the foods of the invention, the amount of β-glucan can be at least about 2 grams per 100 g of a food product. Preferably, the amount of β-glucan in food products for adult consumers is between about 2 to 8 grams per 100 g of a food product. For infant consumers, the amount of β-glucan can be at least about 0.5 grams per 100 g of a food product. Preferably, the amount of β-glucan in food products for infant consumers is between about 0.5 to 3 grams per 100 g of a food product. For example, a food product can contain, per 50 ml or per 50 g of the food product, at least $10^6$ probiotic organisms (e.g., LGG bacteria) and at least 0.5 grams of β-glucan isolated from a natural source.

Any of the preparations described herein may be administered once daily. Alternatively, preparations may be administered twice daily, three times daily, or up to five times daily. An example of an appropriate capsule is a 250 mg gelatin capsule containing about 10 to 100 mg of LGG lyophilized powder ($10^8$ to $10^9$ bacteria), 160 mg microcrystalline cellulose, 77.5 mg gelatin, and 2.5 mg magnesium saturate along with about 0.5 to 8 grams of partially purified β-glucan isolated from an oat or barley source. In another embodiment, a suppository cartridge could contain about 10 to 100 mg of pure LGG powder mixed with about 0.5 to 8 grams of β-glucan. In order to prevent a reaction between LGG and β-glucan the individual suppository would be dry (less than 0.1% moisture). An ointment of the invention can contain, in an amount of ointment normally used for treatment (e.g., in an amount between 1 g and 100 g), about 10 to 100 mg of LGG lyophilized powder ($10^6$ to $10^9$ bacteria) and about 0.5 to 8 grams of β-glucan.

Also envisioned is a packaged food product that includes at least a first and a second compartment isolated from each other by an intermediate partition or seal that prevents mixing of the contents of the compartments. The first compartment can include a composition containing a probiotic and the second compartment can include a composition containing an isolated β-glucan (in the amounts discussed above). The package is constructed to permit mixing of the two compositions in the package, e.g., by a consumer prior to consumption of the mixed food product. The package can include a tube with at least two compartments that are separated by a seal that is more readily broken than the seal forming the periphery of the package, i.e., a "burst" seal. After purchase by the consumer, the consumer applies sufficient pressure to the tube to burst the seal separating the two compartments. Once the seal is broken, the two compositions in the separate compartments can be mixed by the consumer. Preferably, the β-glucan-containing composition is maintained in a dry state, such as in powder form, and the probiotic-containing composition is a liquid or semi-solid food, such as a dairy or non-dairy food (e.g., yogurt, butter, cheese, infant formula, or ice cream). The packaged food product can be prepared according to techniques known in the art, such as those described in U.S. Patent Application Publication No. 20020150658 and U.S. Pat. No. 4,874,618, each of which is incorporated by reference.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A composition comprising, per 100 g of said composition, at least $10^6$ Lactobacillus rhamnosus GG (LGG) having ATCC Accession No. 53103 and at least 0.5 grams of β-glucan isolated from a natural source and having a form that is present in said natural source, wherein, prior to consumption of said composition, less than 10% by weight of said β-glucan is fermented.

2. The composition of claim 1, wherein said β-glucan is isolated from a plant.

3. The composition of claim 2, wherein said plant is a cereal.

4. The composition of claim 3, wherein said cereal is oat, barley, wheat, rye, maize, quinoa, millet, buckwheat, rice, wild rice, or spelt.

5. The composition of claim 1, wherein said composition further comprises whey protein, flavors or flavor masking agents, sweeteners, vitamins, or dietary supplements.

6. A container comprising first and second compartments, wherein said first compartment comprises at least $10^6$ Lactobacillus rhamnosus GG (LGG having ATCC Accession No. 53103 and said second compartment comprises at least 0.5 grams of β-glucan isolated from a natural source and having a form that is present in said natural source, wherein less than 10% by weight of said β-glucan is fermented and wherein said first and second compartments are separated from each other by a partition which prevents mixing of said first and second compartments.

7. The container of claim 6, wherein said partition comprises a burst seal.

8. The composition of claim 1, wherein said β-glucan is at least 10% pure by weight.

9. The composition of claim 8, wherein said β-glucan is at least 40% to 99% pure by weight.

10. The composition of claim 8, wherein said β-glucan is at least 70% pure by weight.

11. The composition of claim 1, wherein said composition comprises 2.0 to 8.0 grams of said β-glucan per 100 grams of said composition.

12. The composition of claim 1, wherein less than 5% by weight of said β-glucan is fermented.

13. The composition of claim 12, wherein less than 1% by weight of said β-glucan is fermented.

14. The composition of claim 1, wherein said composition is formulated as a capsule, tablet, powder, cream, ointment, suppository, or vaccine adjuvant.

15. The composition of claim 14, wherein said capsule, tablet, or suppository comprises between 10 to 100 mg of a powder comprising said LGG, wherein said powder comprises $10^9$ to $10^{11}$ LGG per gram.

16. A method of preparing a probiotic-enhanced composition, said method comprising the steps of:
admixing, per 100 g of said probiotic-enhanced composition, at least $10^6$ Lactobacillus rhamnosus GG having ATCC Accession No. 53103 with and at least 0.5 grams of β-glucan isolated from a natural source and having a form that is present in said natural source to form a probiotic mixture, wherein said probiotic-enhanced composition comprises said admixture, and wherein, prior to consumption of said probiotic-enhanced food composition, less than 10% by weight of said β-glucan is fermented.

17. A method of altering the bacterial flora of the gut comprising orally administering the composition of claim 1 to a human.

18. The method of claim 17, wherein said method treats a gut disorder in said human.

19. The method of claim 18, wherein said gut disorder is irritable bowel syndrome, inflammatory bowel disease, a stomach ulcer, pouchitis, Helicobacter pylori infection, or diarrhea.

20. The method of claim 17, wherein said β-glucan is isolated from a cereal selected from the group consisting of oat, barley, wheat, rye, maize, quinoa, millet, buckwheat, rice, wild rice, and spelt.

21. The method of claim 17, wherein said β-glucan is at least 10% pure by weight.

22. The method of claim 21, wherein said β-glucan is at least 40% to 99% pure by weight.

23. The method of claim 21, wherein said β-glucan is at least 70% pure by weight.

24. The method of claim 17, wherein said composition comprises 2.0 to 8.0 grams of said β-glucan per 100 grams of said composition.

25. The method of claim 17, wherein less than 5% by weight of said β-glucan is fermented.

26. The method of claim 25, wherein less than 1% by weight of said βglucan is fermented.

27. The method of claim 17, wherein said composition is formulated as a capsule, tablet, powder, cream, ointment, suppository, or vaccine adjuvant.

28. The method of claim 27, wherein said capsule, tablet, or suppository comprises between 10 to 100 mg of a powder comprising said LGG, wherein said powder comprises $10^9$ to $10^{11}$ LGG per gram.

\* \* \* \* \*

UNITED STATES PATENT AND TRADEMARK OFFICE
CERTIFICATE OF CORRECTION

PATENT NO. : 8,404,228 B2
APPLICATION NO. : 13/184959
DATED : March 26, 2013
INVENTOR(S) : Sherwood L. Gorbach et al.

It is certified that error appears in the above-identified patent and that said Letters Patent is hereby corrected as shown below:

Title Page 2, Under OTHER PUBLICATIONS, column 1, line 2, in Topping et al., replace "St ate" with --State--.

In the Specification:

Column 2, Line 10, replace "health promoting" with --health-promoting--;

Lines 31-32, replace "*lactobacillis*" with --*Lactobacillus*--.

Column 3, Lines 53-54, replace "gastrointenstinal" with --gastrointestinal--;

Line 65, replace "gastrointenstinal" with -- gastrointestinal--.

In the Claims:

Column 6, Claim 16, Lines 48-49, replace "probiotic-enhanced food composition," with --probiotic-enhanced composition--.

Signed and Sealed this
Twenty-fifth Day of June, 2013

Teresa Stanek Rea
*Acting Director of the United States Patent and Trademark Office*